United States Patent
Duque et al.

(10) Patent No.: US 10,228,058 B2
(45) Date of Patent: Mar. 12, 2019

(54) SEALS AND SEALING METHODS FOR A SURGICAL INSTRUMENT HAVING AN ARTICULATED END EFFECTOR ACTUATED BY A DRIVE SHAFT

(71) Applicant: INTUITIVE SURGICAL OPERATIONS, INC., Sunnyvale, CA (US)

(72) Inventors: Grant Duque, San Jose, CA (US); Todd E. Murphy, Allentown, PA (US); William A. Burbank, Sandy Hook, CT (US); Gregory W. Dachs, II, San Mateo, CA (US)

(73) Assignee: Intuitive Surgical Operations, Inc., Sunnyvale, CA (US)

(*) Notice: Subject to any disclaimer, the term of this patent is extended or adjusted under 35 U.S.C. 154(b) by 493 days.

(21) Appl. No.: 14/943,564

(22) Filed: Nov. 17, 2015

(65) Prior Publication Data
US 2016/0067002 A1 Mar. 10, 2016

Related U.S. Application Data

(62) Division of application No. 13/397,578, filed on Feb. 15, 2012, now Pat. No. 9,216,062.
(Continued)

(51) Int. Cl.
*A61B 17/29* (2006.01)
*A61B 34/30* (2016.01)
(Continued)

(52) U.S. Cl.
CPC ............ *F16J 15/32* (2013.01); *A61B 34/30* (2016.02); *A61B 34/37* (2016.02); *A61B 2017/2948* (2013.01); *A61B 2034/302* (2016.02)

(58) Field of Classification Search
CPC . F16J 15/32; F16J 15/56; A61B 34/30; A61B 2017/2901; A61B 2017/2902; A61B 2017/2948
See application file for complete search history.

(56) References Cited

U.S. PATENT DOCUMENTS

| | | | |
|---|---|---|---|
| 4,936,842 A | 6/1990 | D'Amelio et al. |
| 5,450,842 A | 9/1995 | Tovey et al. |
| (Continued) | | |

FOREIGN PATENT DOCUMENTS

| | | |
|---|---|---|
| DE | 4220644 C1 | 1/1994 |
| EP | 1905346 A2 | 4/2008 |
| EP | 2095778 A1 | 9/2009 |

OTHER PUBLICATIONS

International Search Report and Written Opinion for Application No. PCT/US2012/025286, dated Jul. 2, 2012, 10 pages.
(Continued)

*Primary Examiner* — Nathan J Jenness

(57) ABSTRACT

Sealing assemblies and methods are disclosed for sealing a surgical instrument having an internal drive shaft subject to lateral displacement. A sealing assembly includes a rigid portion shaped to interface with an instrument shaft of the surgical instrument. A laterally oriented slot is open at a radially perimeter location and configured to receive an o-ring seal via the perimeter location. Apertures are disposed on opposing sides of the slot and open to the slot. The apertures are configured to receive the drive shaft there through and are larger than the drive shaft to accommodate lateral displacement of the drive shaft. The slot includes opposing internal sides spaced to interface with opposed axial surfaces of the o-ring seal. The seal inhibits axial transmission of an insufflated gas and/or bodily fluids while accommodating lateral displacement of the drive shaft.

12 Claims, 13 Drawing Sheets

Related U.S. Application Data

(60) Provisional application No. 61/443,200, filed on Feb. 15, 2011.

(51) Int. Cl.
*A61B 34/37* (2016.01)
*F16J 15/32* (2016.01)

(56) References Cited

U.S. PATENT DOCUMENTS

| | | |
|---|---|---|
| 5,810,876 A | 9/1998 | Kelleher |
| 2009/0216248 A1 | 8/2009 | Uenohara et al. |
| 2012/0209289 A1 | 8/2012 | Duque et al. |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

SEALS AND SEALING METHODS FOR A SURGICAL INSTRUMENT HAVING AN ARTICULATED END EFFECTOR ACTUATED BY A DRIVE SHAFT

CROSS-REFERENCES TO RELATED APPLICATIONS

The present application is a Divisional of U.S. patent application Ser. No. 13/397,578 filed Feb. 15, 2012 (Allowed); which application claims the benefit of U.S. Provisional Appln. No. 61/443,200 filed Feb. 15, 2011; the full disclosures which are incorporated herein by reference in their entirety for all purposes.

BACKGROUND

Minimally-invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally-invasive surgical techniques. Also, patient recovery times, patient discomfort, surgical side effects, and time away from work may also be reduced with minimally-invasive surgery.

A common form of minimally-invasive surgery is endoscopy, and a common form of endoscopy is laparoscopy, which is minimally-invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally-invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three-dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally-invasive procedure and relatively simple in design to reduce possible points of failure. In addition, such mechanisms should provide an adequate range of motion to allow the end effector to be manipulated in a wide variety of positions. Such mechanisms typically include moving components (e.g., control cables, control rods) routed within the instrument shaft of the instrument to transmit actuation force/movement to the end effector.

Non-robotic linear clamping, cutting and stapling devices have been employed in many different surgical procedures. For example, such a device can be used to resect a cancerous or anomalous tissue from a gastro-intestinal tract. Unfortunately, many known surgical devices, including known linear clamping, cutting and stapling devices, often have opposing jaws that may be difficult to maneuver within a patient. For known devices having opposing jaws that are maneuverable within a patient, such devices may not generate sufficient clamping force for some surgical applications (e.g., tissue clamping, tissue stapling, tissue cutting, etc.), which may reduce the effectiveness of the surgical device.

Mechanisms that provide for articulation of an end effector and mechanisms that transmit actuation forces to an end effector can include a collection of components routed within an instrument shaft that supports the end effector. Such components may move laterally within the instrument shaft in response to articulation of the end effector. Such lateral displacement, however, presents significant problems with regard to preventing the insufflated gas and/or bodily fluids from traveling up the instrument shaft, thereby complicating instrument cleaning and/or making it difficult to maintain pneumo-peritineal pressure during use in endoscopic procedures.

Thus, there is believed to be a need for seals and sealing methods that prevent insufflated gas and/or bodily fluids from traveling up an instrument shaft of a laparoscopic surgical instrument that includes a laterally moving mechanism component routed within the instrument shaft.

BRIEF SUMMARY

Seals and sealing methods are disclosed that can accommodate axial and lateral displacement of a drive shaft passing through a seal. The disclosed seals and sealing method can be used, for example, to prevent an insufflated gas and/or bodily fluid from traveling up an instrument shaft of a laparoscopic surgical instrument that includes one or more laterally-displacing internal drive shafts that transmit actuation torque from a proximally-disposed drive source to a distally-disposed articulated end effector. The disclosed seals can further be used to engage and seal additional mechanism components, such as control cables, that are routed within the instrument shaft to the end effector. And the disclosed seals can further be used to splice sections of the instrument shaft, thereby providing a convenient way to install such a seal.

Thus, in a first aspect, a seal is provided for use in a minimally-invasive surgical instrument having an internal drive shaft. The seal includes a substantially rigid portion having an outer perimeter shaped to interface with an instrument shaft of the surgical instrument. The instrument shaft defines a shaft axis. The rigid portion is configured to receive an internal drive shaft mounted axially there through for rotation within the instrument shaft. The seal further includes a first slot oriented laterally to the shaft axis and first and second apertures disposed on opposing sides of the first slot and opening to the first slot. The first slot is open at a first radially perimeter location of the seal and is configured to receive a first o-ring seal via the first perimeter opening. The first slot has opposing internal sides oriented laterally to the shaft axis and spaced to simultaneously interface with opposed axial surfaces of the first o-ring seal, creating face seals on both sides of the first-o-ring. The first and second apertures are larger than the internal drive shaft passing through the first and second apertures, respectively, so as to accommodate lateral displacement of the internal drive shaft relative to the instrument shaft while the internal drive shaft rotates and the first o-ring seal inhibits axial transmission of at least one of an insufflated gas or bodily fluids within the instrument shaft.

The seal can be configured to accommodate a range of lateral displacement of the internal drive shaft relative to the instrument shaft. For example, the first o-ring seal can have a cross-sectional radius of sufficient magnitude so as to accommodate the range of lateral displacement of the internal drive shaft relative to the instrument shaft without having any portion of the opposed axial surfaces of the first o-ring seal move out of contact with the opposing internal sides of the first slot.

The seal can include a molded portion attached to the rigid portion and including the first slot. The molded portion can include a suitably resilient material. For example, the molded portion can include a fluoropolymer. And the molded portion can consist essentially of the fluoropolymer.

The rigid portion can be configured to splice first and second segments of the instrument shaft. For example, the rigid portion can include distal and proximal radially peripheral portions that interface with and align the spliced first and second segments of the instrument shaft.

The seal can be configured to accommodate and engagingly seal one or more additional internal drive shafts. For example, the rigid portion can be configured to receive a second internal drive shaft mounted for rotation within the instrument shaft. The seal can include a second slot oriented laterally to the shaft axis, and third and fourth apertures disposed on opposing sides of the second slot and opening to the second slot. The second slot is open at a second radially perimeter location of the seal and configured to receive a second o-ring seal via the second perimeter opening. The second slot has opposing internal sides oriented laterally to the shaft axis and spaced to simultaneously interface and create face seals with opposed axial surfaces of the second o-ring seal. The third and fourth apertures are larger than the second internal drive shaft passing through the third and fourth apertures, respectively, so as to accommodate lateral displacement of the second internal drive shaft relative to the instrument shaft while the second internal drive shaft rotates and the second o-ring seal inhibits axial transmission of at least one of an insufflated gas or bodily fluids within the instrument shaft.

The seal can also be configured to guide and/or seal a cable or rod routed within the instrument shaft. For example, the rigid portion can include one or more additional apertures, each of which is configured to guide a cable or rod routed within the instrument shaft. And the seal can include a molded portion attached to the rigid portion and including the first and second slots. The molded portion can include corresponding one or more additional apertures, each of which is undersized relative to the cable or rod to provide an interference fit seal for the cable or rod.

In another aspect, a method is provided for sealing a minimally-invasive surgical instrument having an internal drive shaft against an insufflated gas and bodily fluids. The method includes interfacing an o-ring seal with an external surface of an internal drive shaft mounted for rotation within an instrument shaft of a minimally-invasive surgical instrument. The instrument shaft defines a shaft axis. The method further includes interfacing opposed axial surfaces of the o-ring seal with opposing internal sides of a slot oriented laterally to the shaft axis. The method further includes accommodating the internal drive shaft within apertures that are disposed on opposing sides of the slot and are open to the slot.

The method can be used to accommodate lateral displacement of the internal drive shaft relative to the instrument shaft. For example, the apertures can be larger than the internal drive shaft passing through the apertures so as to accommodate lateral displacement of the internal drive shaft relative to the instrument shaft while the internal drive shaft rotates and the o-ring seal inhibits axial transmission of at least one of an insufflated gas or bodily fluids within the instrument shaft. And the o-ring seal can have a cross-sectional radius of sufficient magnitude so as to accommodate a range of lateral displacement of the internal drive shaft relative to the instrument shaft without having any portion of the opposed axial surfaces of the o-ring seal move out of contact with the opposing sides of the slot.

The slot can be formed in a molded material. The molded material can include a suitably resilient material. For example, the molded material can include a fluoropolymer. And the molded material can consist essentially of the fluoropolymer.

The method can be extended to seal one or more additional internal drive shafts. For example, the method can further include interfacing a second o-ring seal with an external surface of a second internal drive shaft mounted for rotation within the instrument shaft, interfacing opposed axial surfaces of the second o-ring seal with opposing internal sides of a second slot, and accommodating the second internal drive shaft within apertures that are disposed on opposing sides of the second slot and are open to the second slot. Like the first slot, the second slot is oriented laterally to the shaft axis.

The method can be used to accommodate lateral displacement of the first and second internal drive shafts relative to the instrument shaft. For example, the apertures can be larger than the first and second internal drive shafts passing through the apertures so as to accommodate lateral displacement of the first and second internal drive shafts relative to the instrument shaft while at least one of the internal drive shafts rotates and the o-ring seals inhibit axial transmission of at least one of an insufflated gas or bodily fluids within the instrument shaft. And each of the o-ring seals can have a cross-sectional radius of sufficient magnitude so as to accommodate a range of lateral displacement of the corresponding internal drive shaft relative to the instrument shaft without having any portion of the opposed axial surfaces of the o-ring seal move out of contact with the opposing sides of the corresponding slot.

In another aspect, a method is provided to inhibit axial flow of at least one of bodily fluids or an insufflated gas within an instrument shaft of a minimally-invasive surgical instrument having an internal drive shaft subject to lateral displacement relative to the instrument shaft. The method includes providing an internal drive shaft suitable for mounting within an instrument shaft of a minimally-invasive surgical instrument; sliding an annular sealing body radially inwardly into a slot of a valve seat within the instrument shaft so that resilient compression of the annular sealing body within the slot induces axial sealing engagement between the annular sealing body and the valve seat; and sliding the internal drive shaft axially through an aperture of the annular sealing body so that resilient expansion of the annular sealing body around the internal drive shaft induces radial sealing engagement between the internal drive shaft and the sealing body such that the sealing body is configured to inhibit axial flow of at least one of bodily fluids or an insufflated gas within the shaft while accommodating rotation of the internal drive shaft, axial displacement of the internal drive shaft, and lateral displacement of the internal drive shaft within the instrument shaft.

The method can further include molding the valve seat to a rigid body that laterally positions an actuation cable within the instrument shaft. For example, the method can include molding the valve seat to a metal body so that the aperture of the annular sealing body and the slot define molded sealing surfaces, the metal body having a cable apertures for axially receiving an actuation cable there through so as to laterally position the cable within the instrument shaft, the molded seat body having a cable sealing aperture providing an interference fit seal with the cable.

For a fuller understanding of the nature and advantages of the present invention, reference should be made to the ensuing detailed description and accompanying drawings.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention can be practiced without the specific details. Furthermore, well-known features may be omitted or simplified in order not to obscure the embodiment being described.

Minimally-Invasive Robotic Surgery

Figure 1:
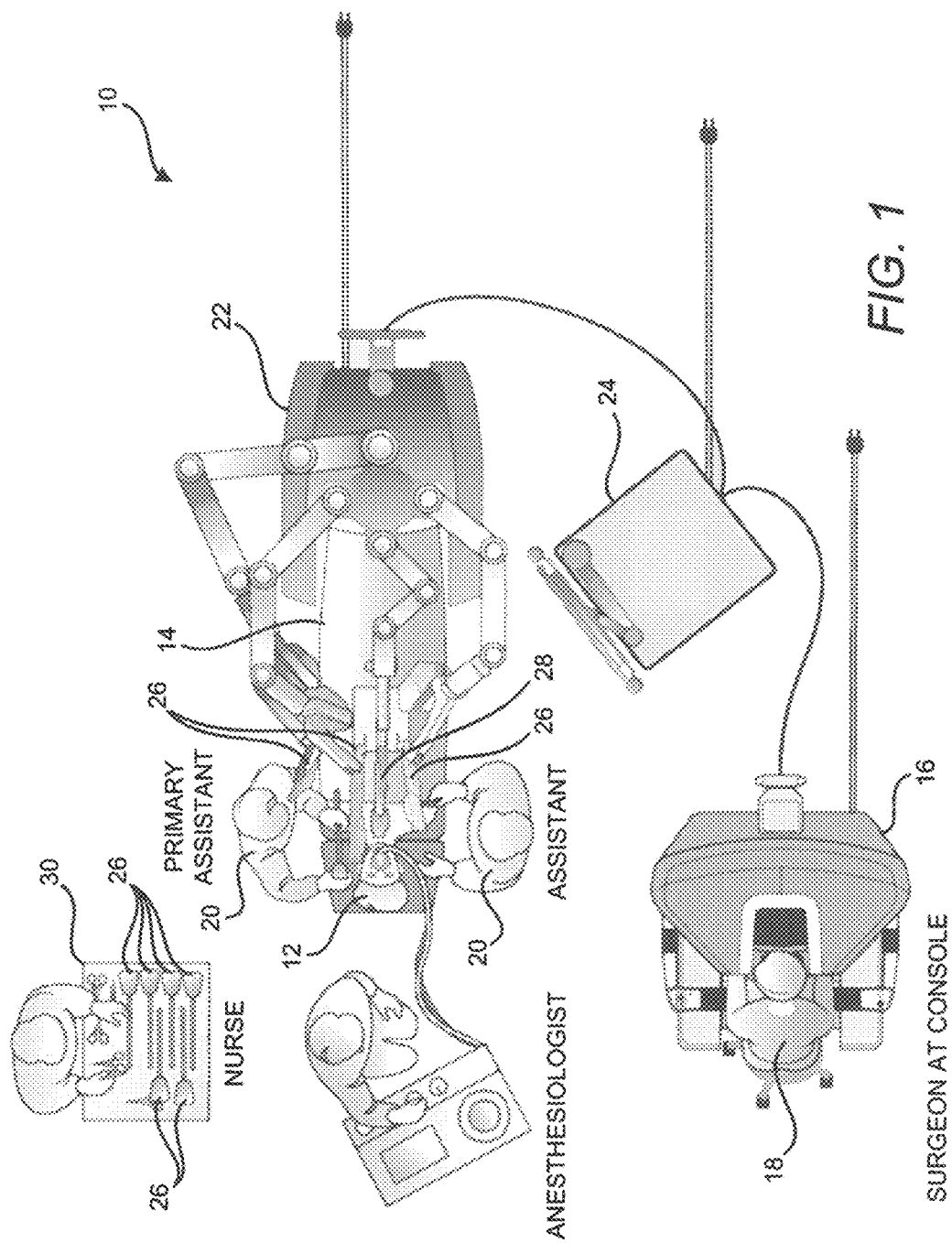
FIG. 1 is a plan view of a minimally-invasive robotic surgery system being used to perform a surgery, in accordance with many embodiments.

Referring now to the drawings, in which like reference numerals represent like parts throughout the several views, FIG. 1 is a plan view illustration of a Minimally-Invasive Robotic Surgical (MIRS) system 10, typically used for performing a minimally-invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient-Side Cart 22 (surgical robot), and an Electronics Cart 24. The Patient Side Cart 22 can manipulate at least one removably coupled tool assembly 26 (hereinafter simply referred to as a "tool") through a minimally-invasive incision in the body of the Patient 12 while the Surgeon 18 views the surgical site through the Console 16. An image of the surgical site can be obtained by an endoscope 28, such as a stereoscopic endoscope, which can be manipulated by the Patient-Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient-Side Cart 22, and replace it with another tool 26 from a tray 30 in the operating room.

Figure 2:
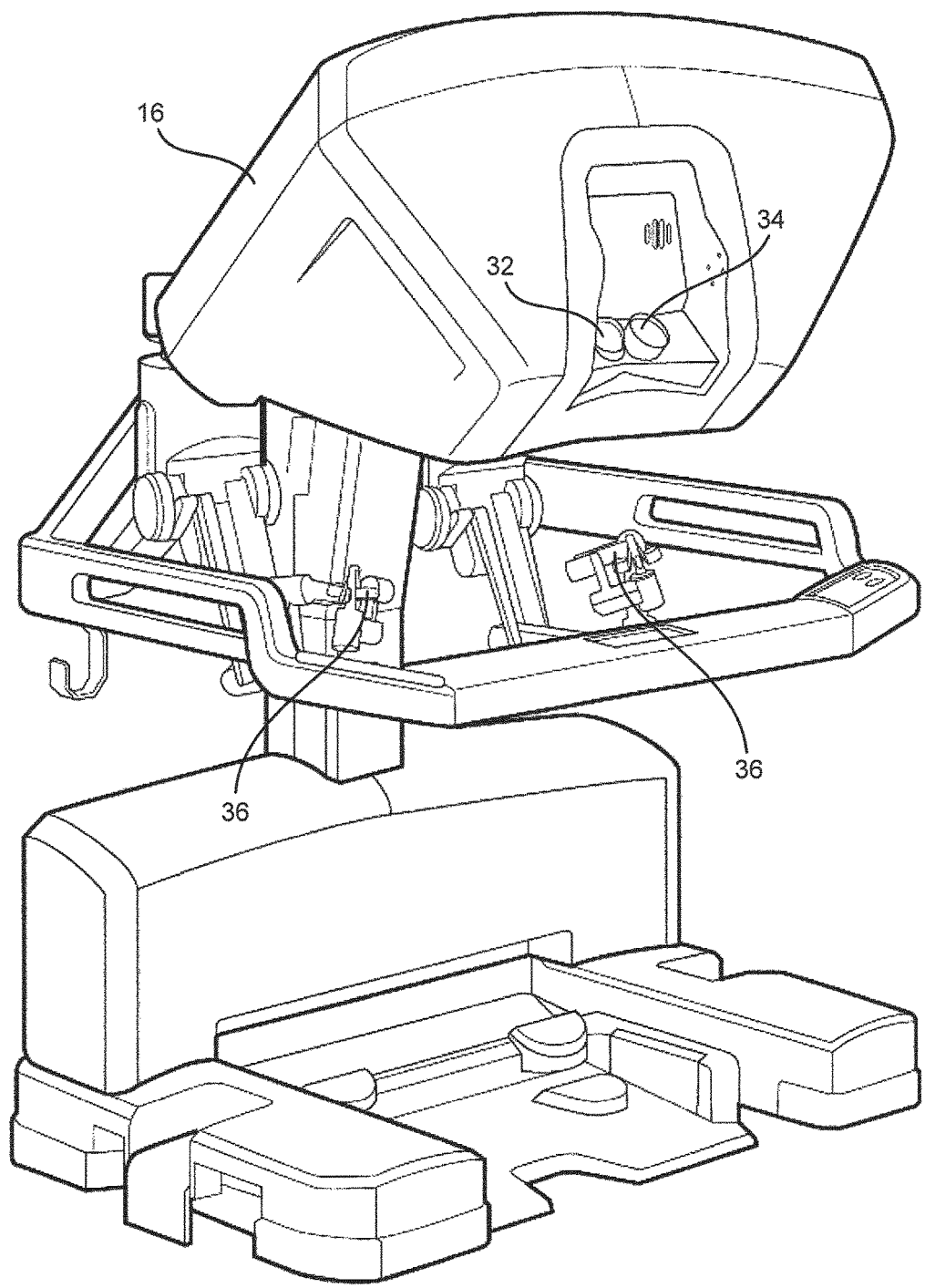
FIG. 2 is a perspective view of a surgeon's control console for a robotic surgery system, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient-Side Cart 22 (shown in FIG. 1) to manipulate one or more tools. The input control devices 36 can provide the same degrees of freedom as their associated tools 26 (shown in FIG. 1) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) can be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures (i.e., operating from outside the sterile field).

Figure 3:
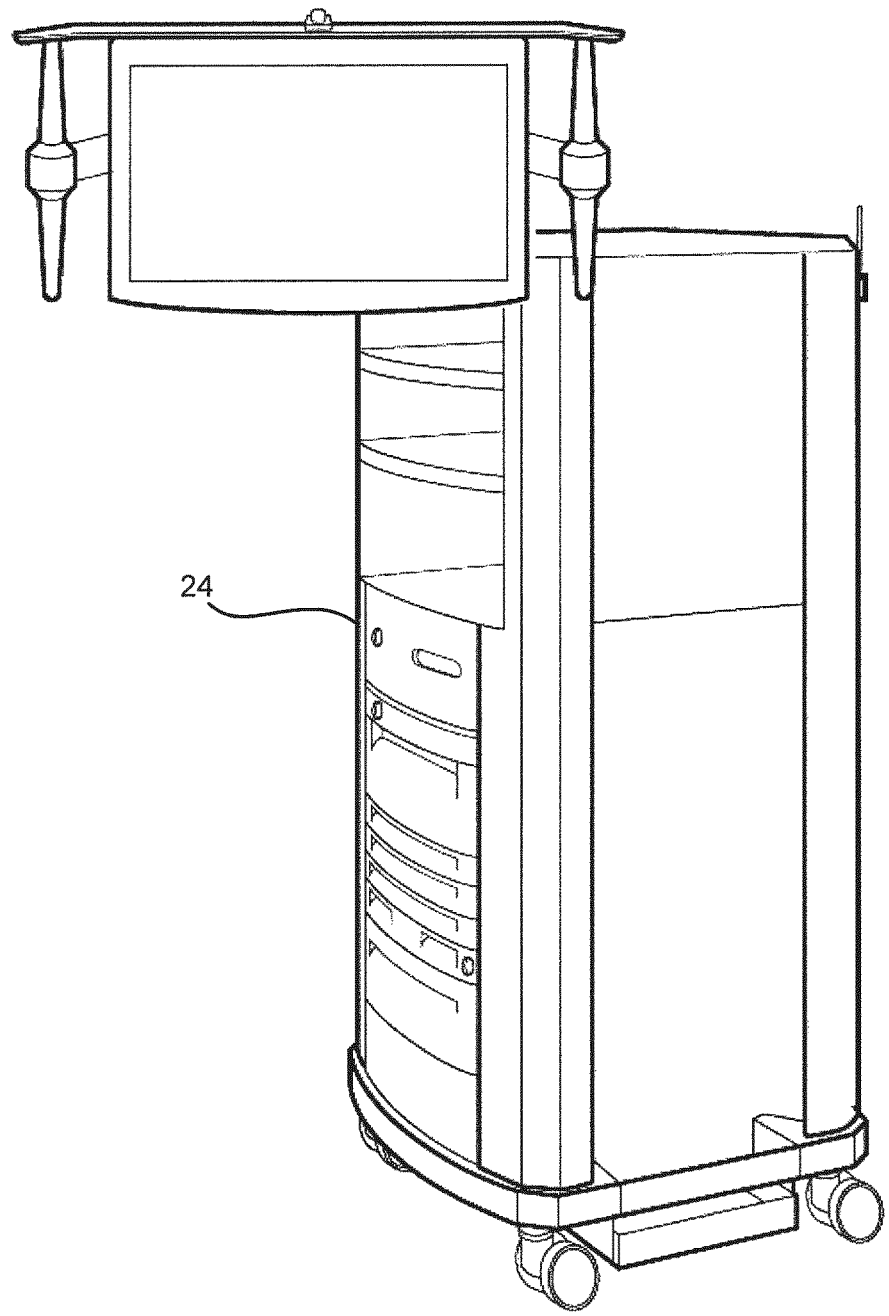
FIG. 3 is a perspective view of a robotic surgery system electronics cart, in accordance with many embodiments.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on any other suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image-capture device, such as optical aberrations.

Figure 4:
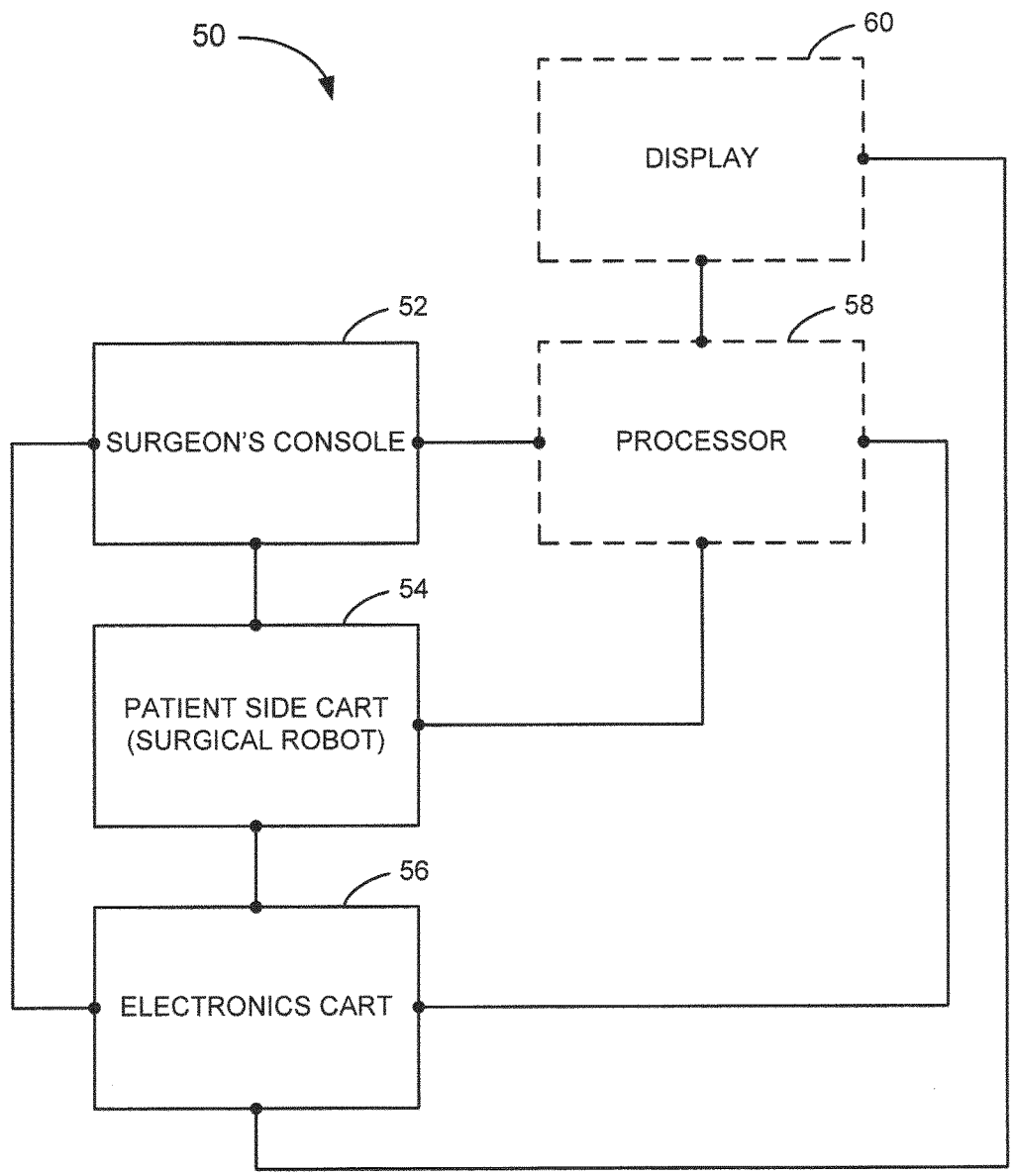
FIG. 4 is a simplified diagrammatic illustration of a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient-Side Cart (Surgical Robot) 54 (such as Patent-Side Cart 22 in FIG. 1) during a minimally-invasive procedure. The Patient-Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient-Side Cart 54 can output the captured images for processing outside the Electronics Cart 56. For example, the Patient-Side Cart 54 can output the captured images to a processor 58, which can be used to process the captured images. The images can also be processed by a combination the Electronics Cart 56 and the processor 58, which can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or any other related images.

Figure 5B:
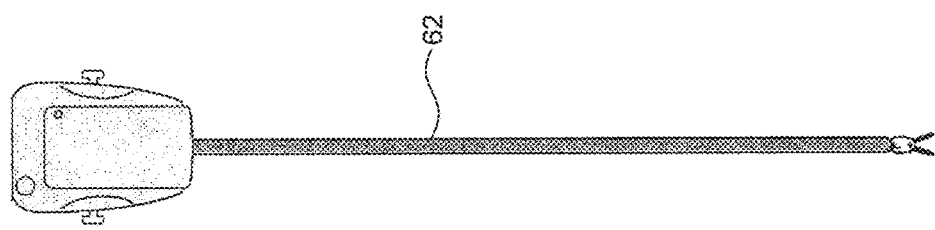
FIG. 5B is a front view of a robotic surgery tool.
Figure 5A:
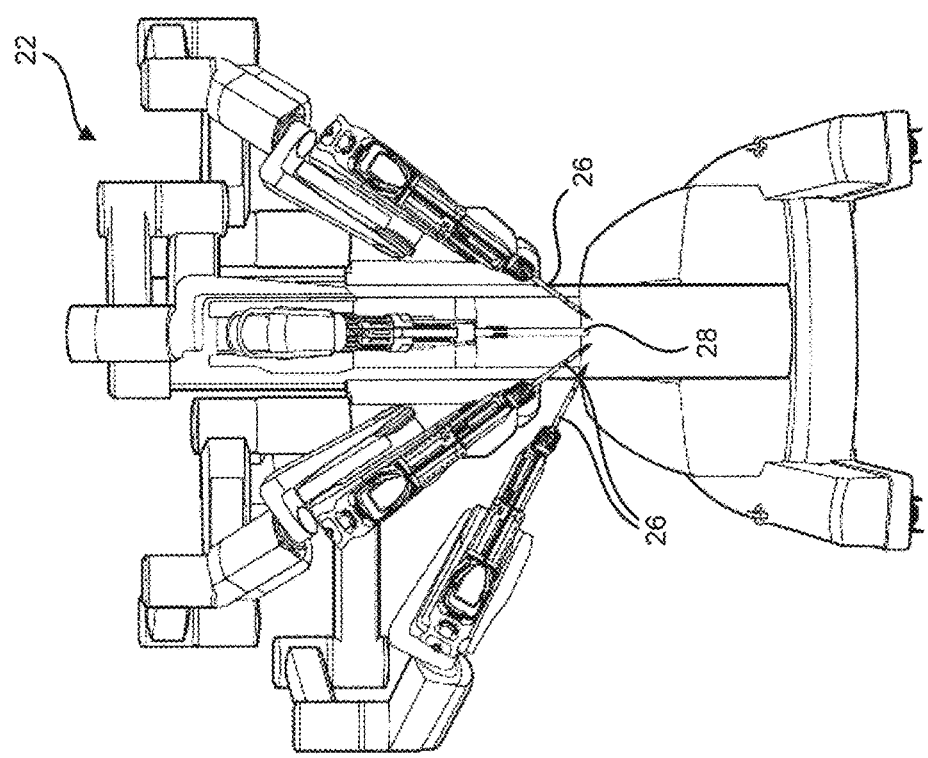
FIG. 5A is a front view of a patient-side cart (surgical robot) of a robotic surgery system, in accordance with many embodiments.

FIGS. 5A and 5B show a Patient-Side Cart 22 and a surgical tool 62, respectively. The surgical tool 62 is an example of the surgical tools 26. The Patient-Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical tools 26 when they are positioned within the field-of-view of the imaging device 28.

Figure 6:
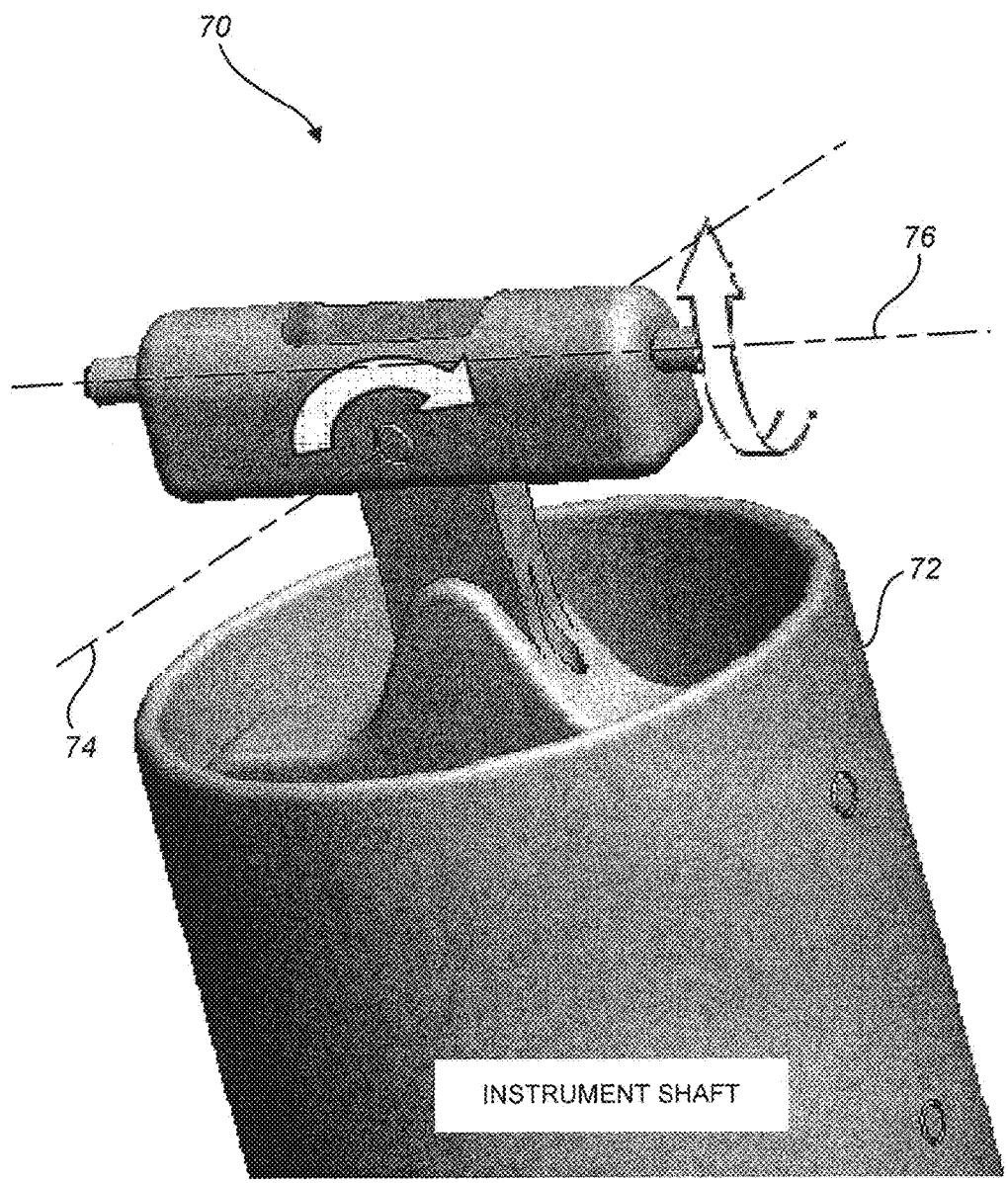
FIG. 6 is a perspective view of an exemplary two degree-of-freedom wrist used to support an end effector disposed at a distal end of an instrument shaft.

FIG. 6 illustrates an exemplary two degree-of-freedom wrist 70 that can be used to support an end effector (not shown) disposed at a distal end of an instrument shaft 72. The wrist 70 provides for rotation of the end effector about perpendicular axes 74, 76. With regard to actuation components routed within the instrument shaft between a proximal actuation assembly and the distal end effector, rotation of the end effector relative to the axes 74, 76 may generate lateral displacement of the actuation components relative to the instrument shaft.

Figure 7:
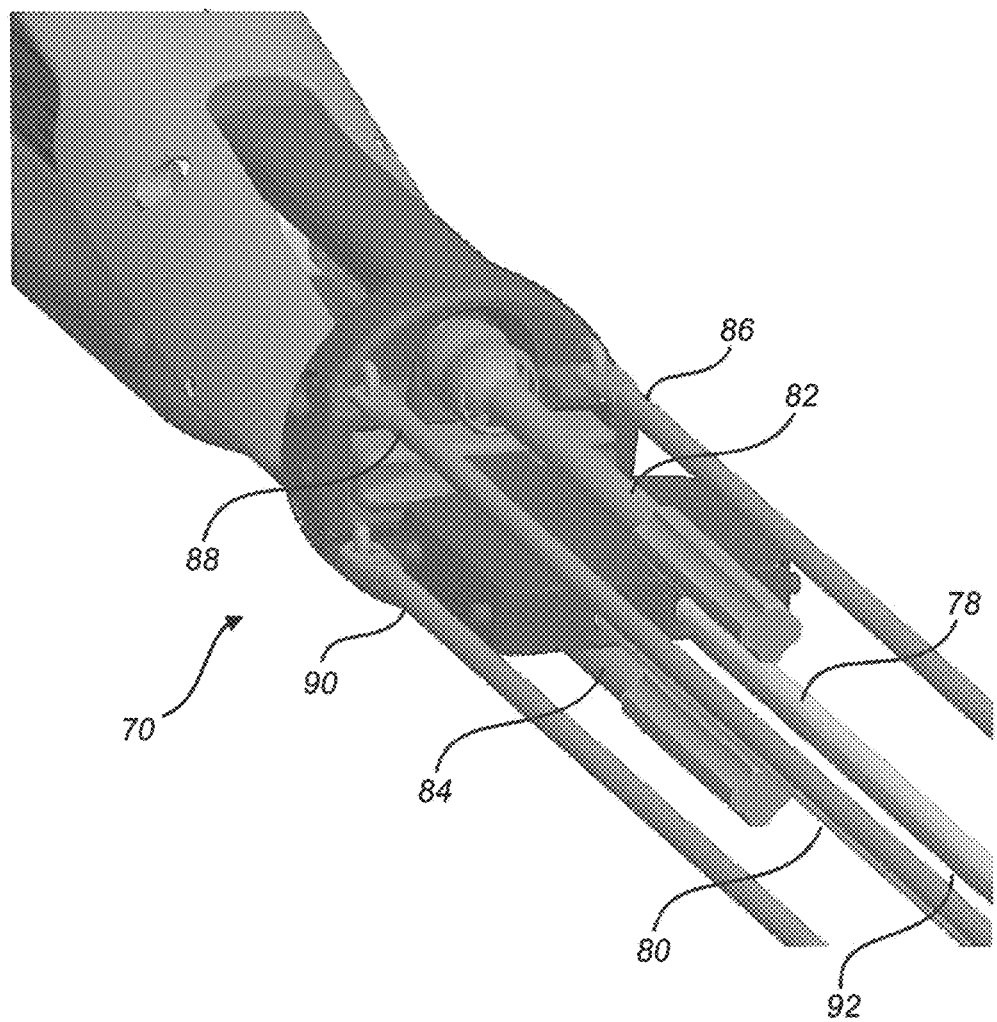
FIG. 7 is a perspective view of the two degree-of-freedom wrist of FIG. 6 and actuation system components coupled to an end effector so as to be subjected to lateral displacement relative to the instrument shaft due to articulation of the end effector.

FIG. 7 is a perspective view of the two degree-of-freedom wrist 70 that illustrates an exemplary routing of actuation system components along two sides of the two degree-of-freedom wrist 70 and routing of control cables 78, 80 through the two degree-of-freedom wrist 70. The actuation system components include a first drive shaft assembly 82 routed above the wrist, a second drive shaft assembly 84 routed below the wrist, end effector articulation pull rods 86, 88, 90, and 92 routed above and below the wrist, and the control cables 78, 80 routed through the wrist. Articulation of the end effector about the two wrist axes generates lateral displacement of the first and second drive shaft assemblies. Such lateral displacement of the first and second drive shaft assemblies can be accommodated by the seals and sealing methods disclosed herein.

Seal Assemblies

Figure 8A:
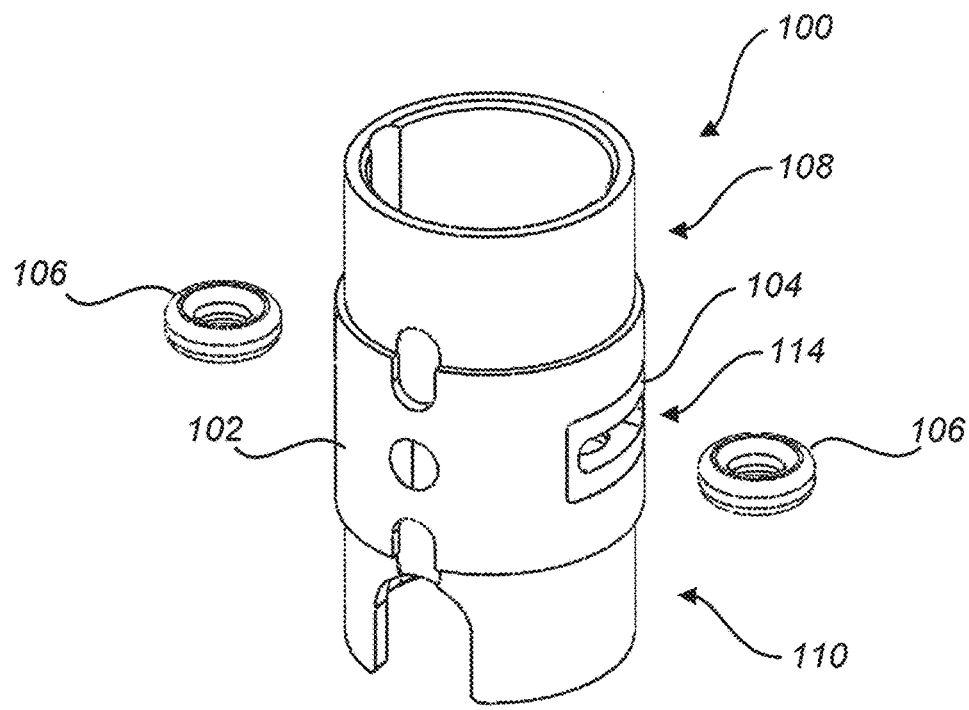
FIG. 8A is a perspective view of a seal assembly, in accordance with many embodiments, showing o-ring seals of the seal assembly offset from associated slots of the seal assembly.
Figure 8B:
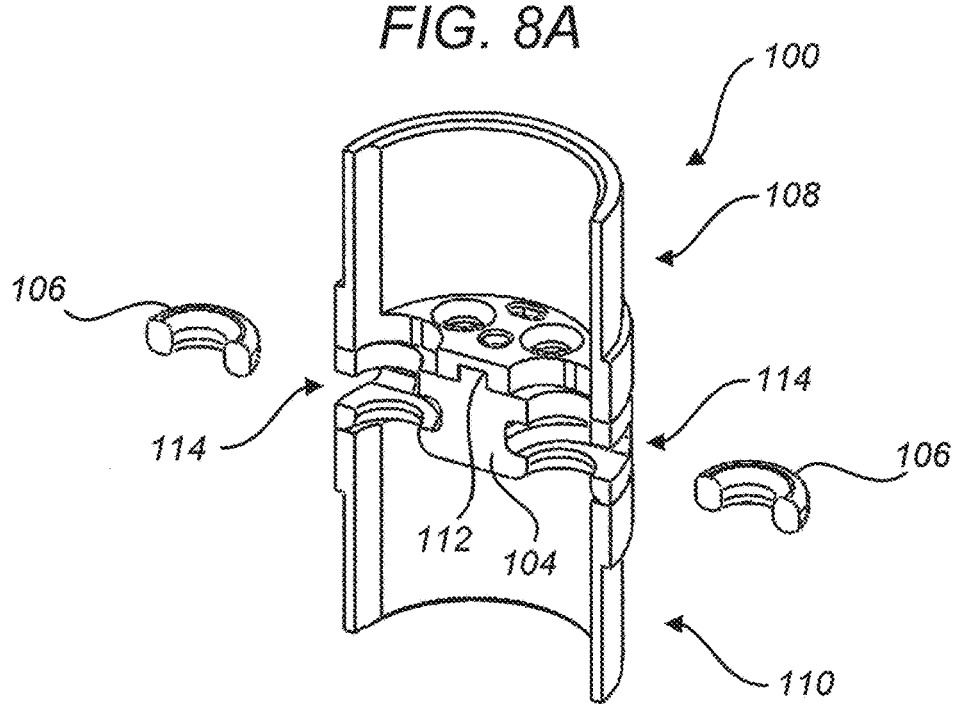
FIG. 8B is a perspective cross-sectional view of the seal assembly of FIG. 8A.

FIGS. 8A and 8B illustrates a seal assembly 100 for an articulating wristed surgical device, which utilizes control rods and rotary drive-shaft components. The seal assembly 100 is particularly useful in sealing such a surgical device against an insufflated gas and/or bodily fluids. The seal assembly 100 includes a substantially rigid portion 102, a molded portion 104 attached to the rigid portion 102, and two o-ring seals 106 (shown displaced from respective slots formed in the molded portion that receive the o-ring seals).

The rigid portion 102 provides a housing for the seal assembly. The rigid portion 102 has an outer perimeter shaped to interface with and splice two instrument shaft segments (not shown), and a bulkhead that has apertures that accommodate two internal drive shafts, six drive rods, and control wires. The outer perimeter includes a distal radially peripheral portion 108 and a proximal radially peripheral portion 110 that are recessed to accommodate and align first and second segments of the instrument shaft. Each of the apertures for the drive shafts are larger than the respective drive shaft passing through the aperture, thereby accommodating lateral displacement of the drive shaft. The apertures for the six drive rods and control wires have flared openings shaped to accommodate different angles of the drive rods relative to the apertures that may occur due to articulation of the end effector. The outer perimeter of the rigid portion includes two apertures that accommodate perimeter portions of the molded portion in which slots in the molded portion are open to the exterior of the seal assembly. The bulkhead also includes a recess 112 that provides additional interface surfaces between the rigid and molded portions, thereby securing a more positive engagement between the rigid and molded portions.

The rigid portion 102 can be made from any suitably rigid material that is compatible with a surgical application. The rigid portion can be fabricated from a metal suitable for a surgical application. For example, the rigid portion can be fabricated from 17-4 PH stainless steel using standard machining processes. The rigid portion can also be fabricated from other stainless steels, such as suitable grades of 300 or 400 series stainless steel. Additionally, the rigid portion can be fabricated using Metal Injection Molding (MIM), which may be economically justified where the number of rigid portions to be fabricated is sufficient to offset the cost of MIM tooling.

The molded portion 104 is molded over the rigid portion 102. During the molding of the molded portion, the rigid portion and additional tooling features (not shown) form a mold for the molded portion 104. The molded portion 104 can be formed from a suitable material, for example, a resilient material that includes a fluoropolymer. The molded portion can also be formed from a material that consists essentially of a fluoropolymer. Suitable materials for the molded portion include Fluoropolymer, Polyfluorocarbon, Kalrez, Buna-N, Santoprene, all of which would preferably possess suitable high-temperature characteristics to tolerate operational temperatures (e.g., localized friction-induced high temperatures) and to survive steam sterilization.

The molded portion 104 includes slots 114 configured to receive the o-ring seals 106. The slots 114 are oriented laterally to a shaft axis 116 (illustrated in FIG. 9) defined by an instrument shaft 118 (partially illustrated in FIG. 9). The slots 114 are open radially perimeter locations of the molded portion 104. And the radially perimeter locations are aligned with the apertures of the rigid portion such that the slots are open to radially perimeter locations of the seal assembly. Each of the slots include opposing internal sides oriented laterally to the shaft axis 116 and spaced to simultaneously interface with obverse and reverse annular sealing surfaces 120 of the respective o-ring seal.

The molded portion 104 includes drive shaft apertures 122 configured to receive the internal drive shafts axially there through. The drive shaft apertures 122 are disposed on opposing sides of the slots and open to the slots. The drive shaft apertures 122 are larger than the internal drive shafts passing there through so as to accommodate lateral displacement of the internal drive shafts relative to the instrument shaft while the internal drive shafts rotate and the o-ring seals inhibit axial transmission of at least one of an insufflated gas or bodily fluids within the instrument shaft.

The molded and rigid portions further includes six apertures that accommodate and seal around the four pull rods and the two control cables. Each of the six control rod apertures in the molded portion 104 are undersized relative to the respective control rod to provide an interference fit seal for the control rod.

Figure 9:
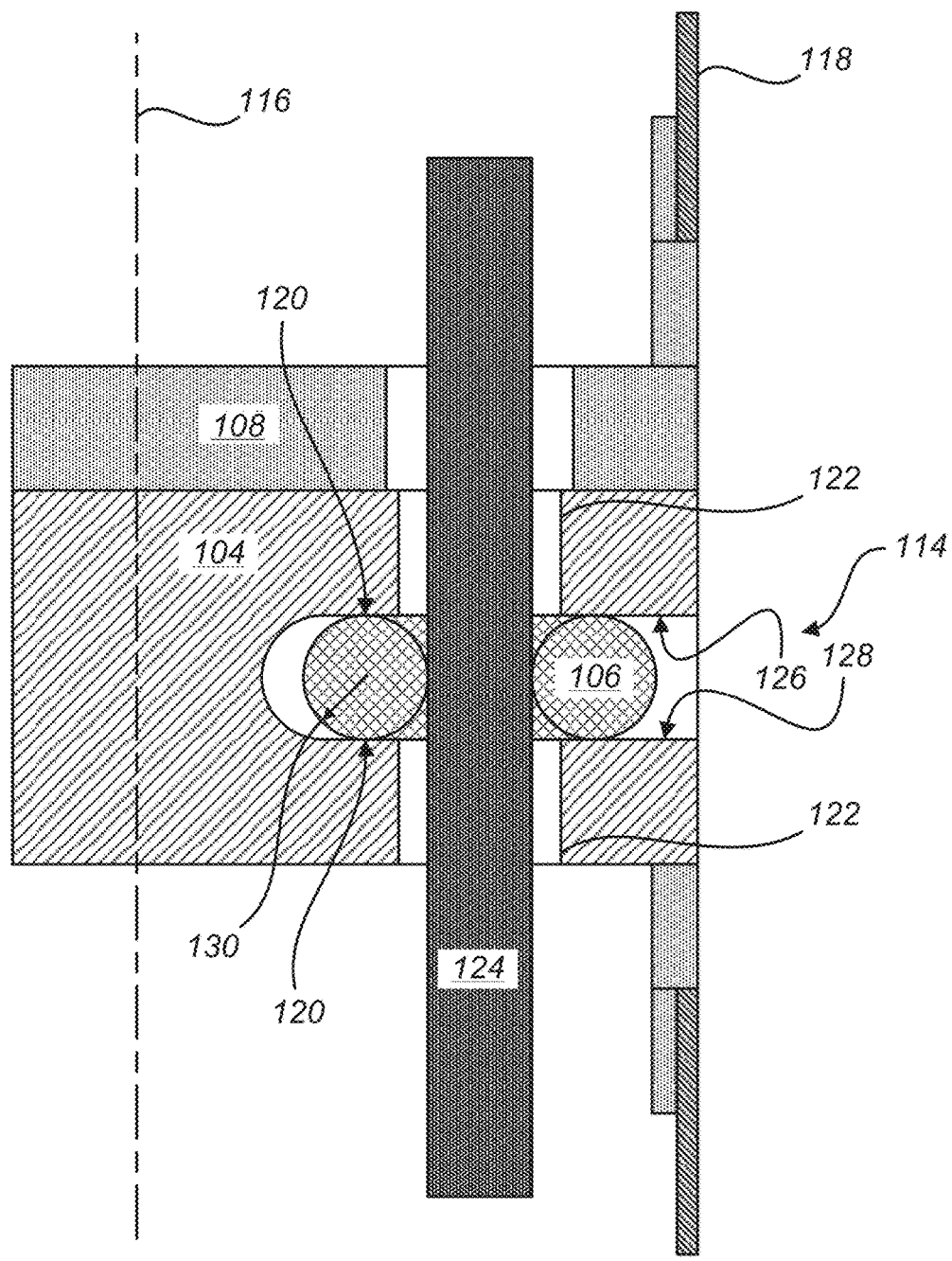
FIG. 9 is a simplified cross-sectional view illustrating the sealing of an internal drive shaft subject to lateral displacement relative to an instrument shaft, in accordance with many embodiments.

FIG. 9 is a simplified cross-sectional view further illustrating how the seal assembly seals a drive shaft 124 subject to lateral displacement. The drive shaft 124 is received within the o-ring seal 106, thereby providing a circular sealing interface where the o-ring seal 106 contacts the drive shaft 124. The o-ring seal 106 is received within the slot 114 in the molded portion 104. The slot 114 has opposing internal sides 126, 128, which are oriented laterally to the shaft axis 116 defined by the instrument shaft 118 and spaced apart to simultaneously interface with the obverse and reverse annular sealing surfaces 120 of the o-ring seal 106, thereby providing offset circular sealing interfaces wherein the o-ring seal 106 contacts the opposing internal sides 126, 128 of the slot 114 in the molded portion 104. The apertures 122 in the molded portion are larger than the drive shaft 124 passing through the apertures 122, thereby accommodating lateral displacement of the drive shaft 124. And the o-ring seal 106 has a cross-sectional radius 130 that is suitably larger than a nominal gap between the apertures 122 in the molded portion and the drive shaft 124 so as to accommodate a range of lateral displacement of the drive shaft 124 relative to the instrument shaft 118 without having any portion of the obverse and reverse annular sealing surfaces 120 move out of contact with the corresponding opposing internal side of the slot. For example, the cross-sectional radius can be equal to or greater than twice the nominal gap, thereby accommodating a range of lateral displacement of the drive shaft 124 relative to the instrument shaft equal to the nominal gap without having any portion of each of the obverse and reverse annular sealing surfaces 120 move out of contact with the respective opposing internal side of the slot.

Figure 10:
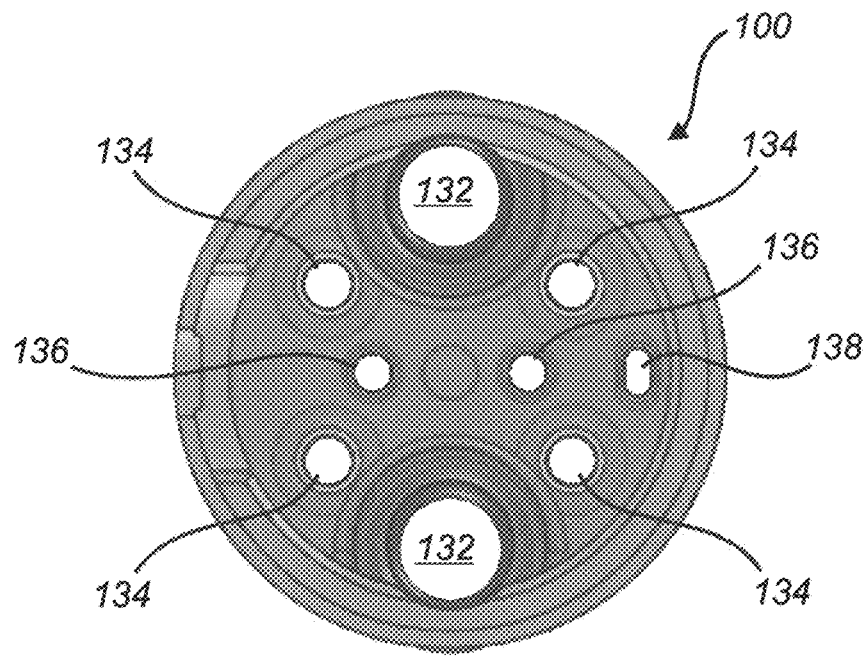
FIG. 10 is an end view of the seal assembly of FIG. 8A, showing sealing provisions for two internal drive shafts subject to lateral displacement, four end effector wrist articulation members, two control cables, and control wires.
Figure 11:
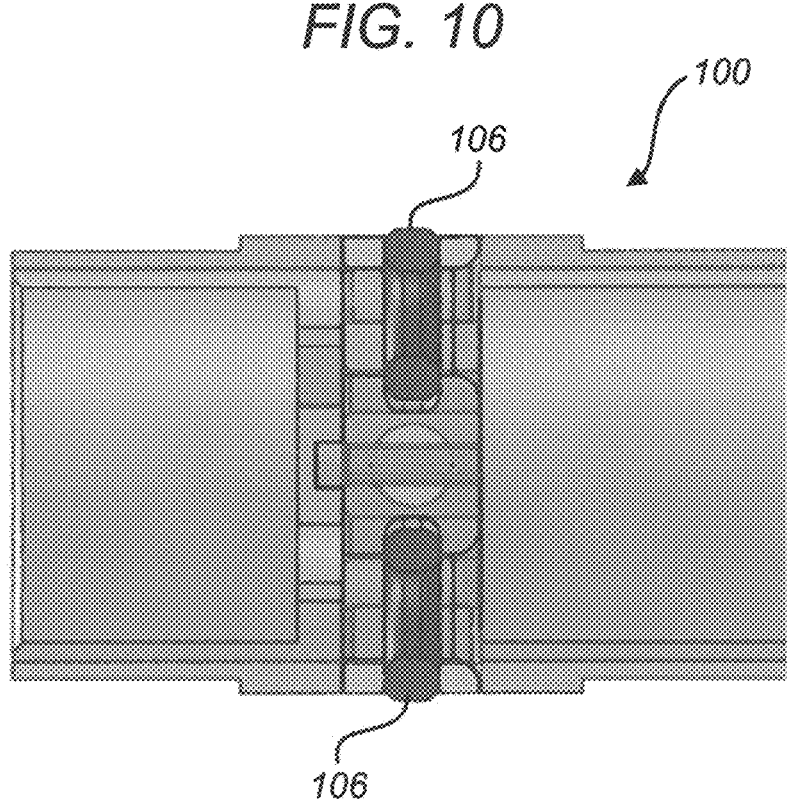
FIG. 11 is a cross-sectional view of the seal assembly of FIG. 8A, showing the o-ring seals disposed in respective slots in the molded portion of the seal.
Figure 12:
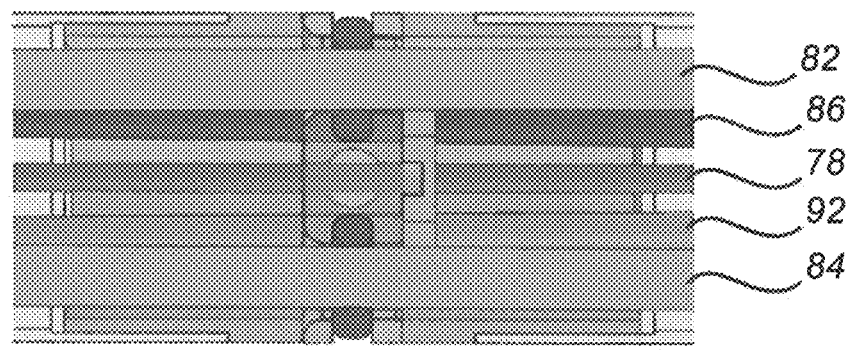
FIG. 12 is a cross-sectional view of the seal assembly of FIG. 8A, showing the locations of end effector actuation and articulation components that pass through the seal assembly.
Figure 13:
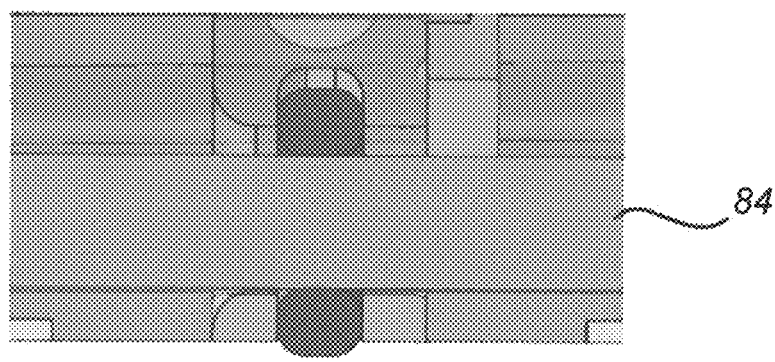
FIG. 13 is a cross-sectional close-up view of the seal assembly of FIG. 8A, showing an internal drive shaft disposed at a lower limit of lateral displacement.
Figure 14:
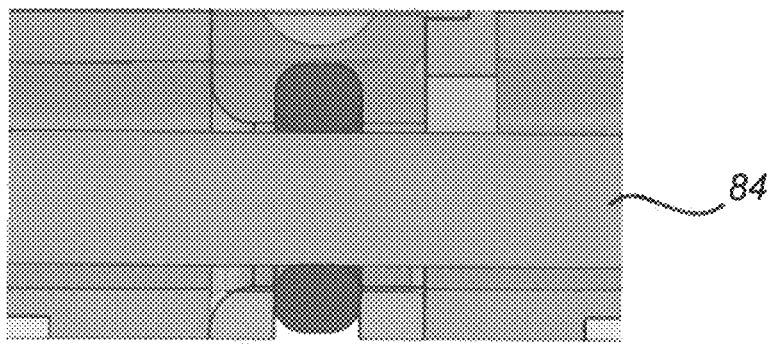
FIG. 14 is a cross-sectional close-up view of the seal assembly of FIG. 8A, showing the internal drive shaft of FIG. 13 disposed at an upper limit of lateral displacement.

FIG. 10 through FIG. 14 further illustrate the seal assembly 100. FIG. 10 is an end view of the seal assembly 100, showing sealing provisions 132 for two drive shafts subject to lateral displacement, sealing provisions 134 for four end effector wrist articulation members, sealing provisions 136 for two control cables, and a sealing provision 138 for control wires. FIG. 11 is a cross-sectional view of the seal assembly 100, showing the o-rings seals 106 disposed in respective slots in the molded portion of the seal assembly. FIG. 12 is a cross-sectional view of the seal assembly of FIG. 8A, showing the locations of components that pass through the seal, specifically the two laterally displacing drive shafts 82, 84, two of the four end effector wrist articulation members 86, 92, and one of the two control cables 78. FIG. 13 is a cross-sectional close-up view of the seal assembly 100, showing the drive shaft 84 disposed at a lower limit of lateral displacement. And FIG. 14 is a cross-sectional close-up view of the seal assembly 100, showing the drive shaft 84 disposed at an upper limit of lateral displacement.

Sealing Methods

Figure 15:
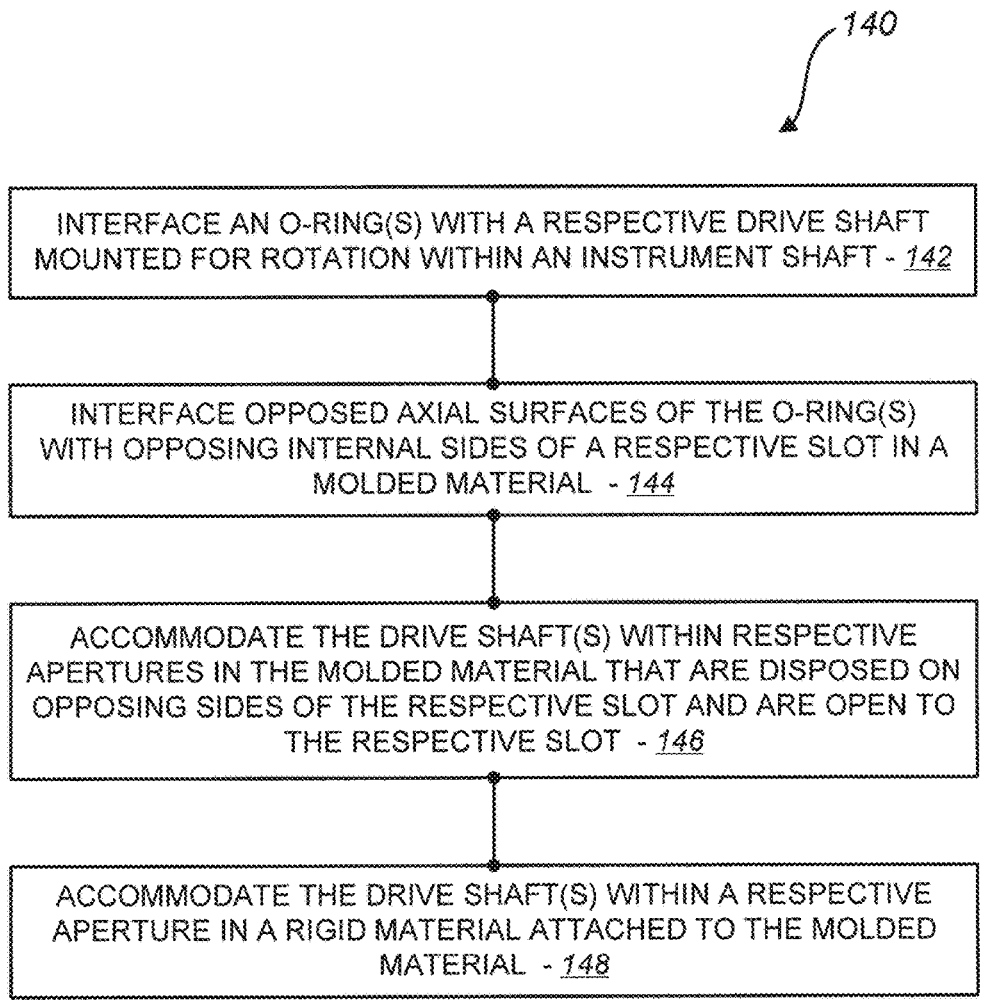
FIG. 15 is a simplified block diagram of a method for sealing a minimally-invasive surgical instrument having an internal drive shaft against an insufflated gas and bodily fluids, in accordance with many embodiments.

FIG. 15 illustrates a method 140 for sealing a minimally-invasive surgical instrument having an internal drive shaft against an insufflated gas and bodily fluids, in accordance with many embodiments. The seal assemblies disclosed herein can be used to practice the method 140. And the method 140 can be used to seal a surgical instrument having one or more internal drive shafts. In step 142, an o-ring is interfaced with an external surface of an internal drive shaft mounted for rotation within an instrument shaft of a minimally-invasive surgical instrument. The instrument shaft defines a shaft axis. In step 144, opposed axial surfaces of the o-ring are interfaced with opposing internal sides of a slot in a molded material. The slot is oriented laterally to the shaft axis. In step 146, the internal drive shaft is accommodated within apertures in the molded material that are disposed on opposing sides of the slot and are open to the slot. In optional step 148, the internal drive shaft is accommodated within a respective aperture in a rigid material (e.g., a metal suitable for surgical applications) attached to the molded material.

The method 140 can be used when the internal drive shaft is subject to lateral displacement relative to the shaft axis. For example, the apertures in the molded material can be larger than the internal drive shaft passing through the apertures so as to accommodate lateral displacement of the internal drive shaft relative to the instrument shaft while the internal drive shaft rotates and the o-ring inhibits axial transmission of at least one of an insufflated gas or bodily fluids within the instrument shaft. The o-ring can have a cross-sectional radius of sufficient magnitude so as to accommodate a range of lateral displacement of the internal drive shaft without having any portion of the opposed axial surfaces of the o-ring move out of contact with the opposing internal sides of the slot.

A suitable molded material can be used to practice the method 140. For example, the molded material can include a fluoropolymer. And the molded material can consist essentially of a fluoropolymer.

Figure 16:
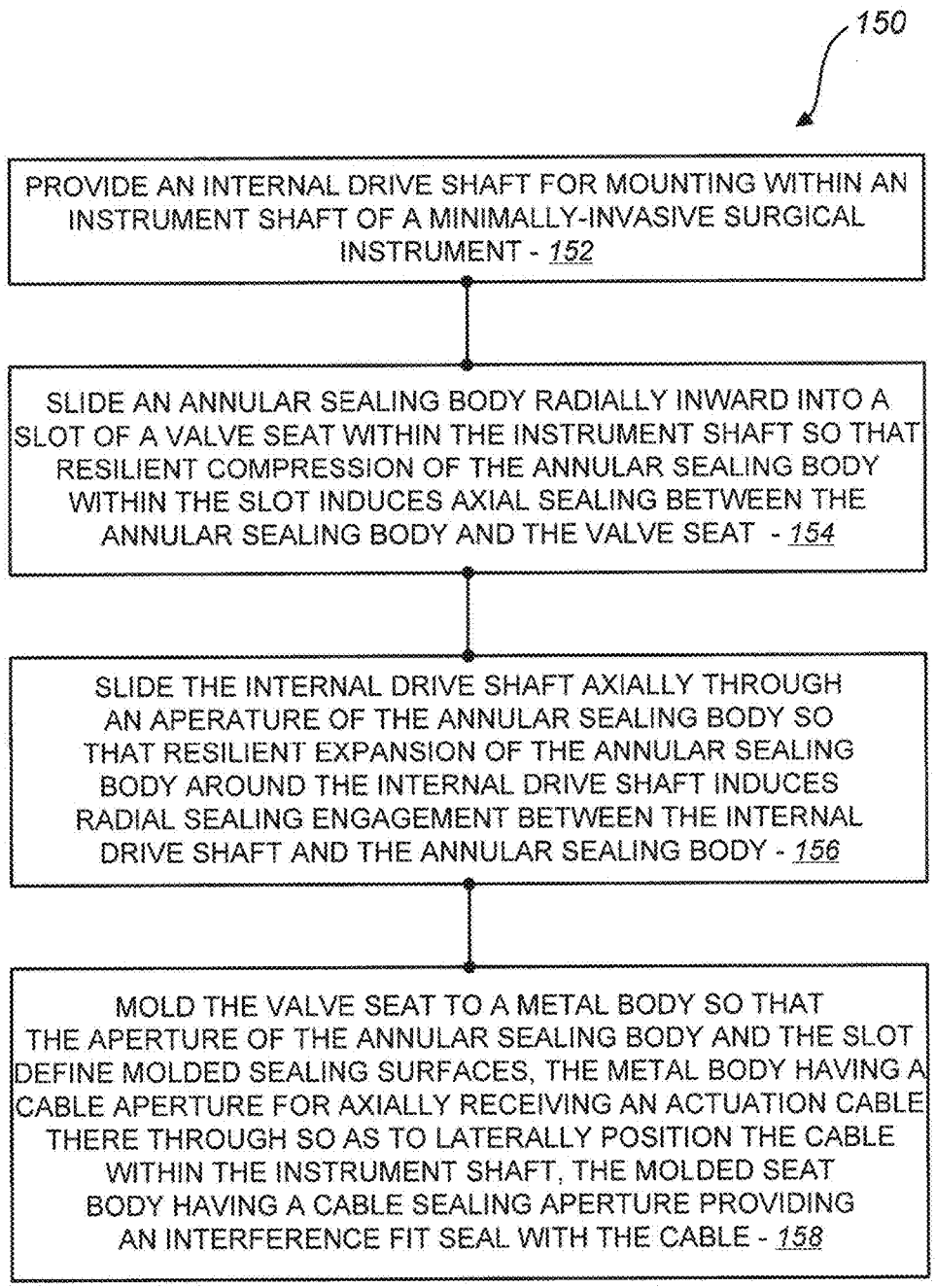
FIG. 16 is a simplified block diagram of another method for sealing a minimally-invasive surgical instrument having an internal drive shaft against an insufflated gas and bodily fluids, in accordance with many embodiments.

FIG. 16 illustrates a method 150 in accordance with many embodiments. The seal assemblies disclosed herein can be used to practice the method 150. And the method 150 can be used to seal a surgical instrument having one or more internal drive shafts. In step 152, an internal drive shaft is provided that is suitable for mounting within an instrument shaft of a minimally-invasive surgical instrument. The instrument shaft defines an axis. In step 154, an annular sealing body is slid radially inward into a slot of a valve seat within the instrument shaft so that resilient compression of the annular sealing body within the slot induces axial sealing engagement between the annular sealing body and the valve seat. For example, as illustrated in FIG. 9, the o-ring seal 106 (i.e., annular sealing body) can be slid radially inward into the slot 114 in the molded portion 104 (i.e., valve seat) so that resilient compression of the o-ring seal 106 within the slot induces axial sealing engagement between the o-ring seal 106 and the molded portion 104. In step 156, the internal drive shaft is slid axially through an aperture of the annular sealing body so that resilient expansion of the annular sealing body around the internal drive shaft induces radial sealing engagement between the internal drive shaft and the sealing body such that the sealing body is configured to inhibit axial flow of at least one of bodily fluids or an insufflated gas within the shaft while accommodating rotation of the internal drive shaft, axial displacement of the internal drive shaft, and lateral displacement of the internal drive shaft within the instrument shaft. In optional step 158, the valve seat can be molded to a metal body so that the aperture of the annular sealing body and the slot define molded sealing surfaces. The metal body can have a cable aperture for axially receiving an actuation cable there through so as to laterally position the cable within the instrument shaft. And the molded valve seat can have a cable sealing aperture providing an interference fit seal with the cable.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method for sealing a minimally-invasive surgical instrument including a first internal drive shaft against at least one of an insufflated gas or bodily fluids, the method including:
    interfacing a first O-ring seal with an external surface of a first internal drive shaft mounted for rotation within an instrument shaft of a minimally-invasive surgical instrument, the instrument shaft defining a shaft axis;
    interfacing opposed axial surfaces of the first O-ring seal with opposing internal sides of a first slot oriented laterally to the shaft axis and formed in a seal assembly coupled to the instrument shaft, the first slot being sized to accommodate lateral sliding of the first O-ring seal in the first slot; and
    accommodating the first internal drive shaft within first and second apertures formed in the seal assembly that are disposed on opposing sides of the first slot and are open to the first slot.

2. The method of claim 1, wherein each of the first and second apertures is larger than the first internal drive shaft passing through the first and second apertures so as to accommodate lateral displacement of the first internal drive shaft relative to the instrument shaft while the first internal drive shaft rotates and the first O-ring seal inhibits axial transmission of at least one of an insufflated gas or bodily fluids within the instrument shaft.

3. The method of claim 2, wherein the first O-ring seal has a cross-sectional radius of sufficient magnitude so as to accommodate a range of lateral displacement of the first internal drive shaft relative to the instrument shaft without having any portion of the opposed axial surfaces of the first O-ring seal move out of contact with the opposing internal sides of the first slot.

4. The method of claim 1, wherein the first slot is formed in a molded material.

5. The method of claim 4, wherein the molded material comprises a fluoropolymer.

6. The method of claim 5, wherein the molded material consists essentially of the fluoropolymer.

7. The method of claim 1, further comprising:
   interfacing a second O-ring seal with an external surface of a second internal drive shaft mounted for rotation within the instrument shaft;
   interfacing opposed axial surfaces of the second O-ring seal with opposing internal sides of a second slot oriented laterally to the shaft axis and formed in the seal assembly, the second slot being sized to accommodate lateral sliding of the second O-ring seal in the second slot; and
   accommodating the second internal drive shaft within third and fourth apertures formed in the seal assembly that are disposed on opposing sides of the second slot and are open to the second slot.

8. The method of claim 7, wherein each of the third and fourth apertures is larger than the second internal drive shaft passing through the third and fourth apertures so as to accommodate lateral displacement of the second internal drive shaft relative to the instrument shaft while the second internal drive shaft rotates and the second O-ring seal inhibits axial transmission of at least one of an insufflated gas or bodily fluids within the instrument shaft.

9. The method of claim 8, wherein each of the first and second O-ring seals has a cross-sectional radius of sufficient magnitude so as to accommodate a range of lateral displacement of the corresponding one of the first and second internal drive shafts relative to the instrument shaft without having any portion of the opposed axial surfaces of the O-ring seal move out of contact with the opposing internal sides of the corresponding one of the first and second slots.

10. The method of claim 1, wherein interfacing the opposed axial surfaces of the first O-ring seal with the opposing internal sides of the first slot comprises sliding the first O-ring seal radially inwardly into the first slot so that resilient compression of the first O-ring seal within the first slot induces axial sealing engagement between the first O-ring seal and the opposing internal sides of the first slot.

11. The method of claim 1, wherein interfacing the first O-ring seal with the external surface of the first internal drive shaft comprises sliding the first internal drive shaft axially through an aperture of the first O-ring seal so that resilient expansion of the first O-ring seal around the first internal drive shaft induces radial sealing engagement between the first internal drive shaft and the first O-ring seal such that the first O-ring seal is configured to inhibit axial flow of at least one of bodily fluids or an insufflated gas within the instrument shaft while accommodating rotation of the first internal drive shaft, axial displacement of the first internal drive shaft, and lateral displacement of the first internal drive shaft within the instrument shaft.

12. The method of claim 11, wherein the seal assembly comprises a valve seat molded to a metal body so that the aperture of the first O-ring seal and the first slot define molded sealing surfaces, the metal body having a cable aperture for axially receiving an actuation cable there through so as to laterally position the cable within the instrument shaft, the molded valve seat having a cable sealing aperture providing an interference fit seal with the actuation cable.

* * * * *